United States Patent
Ratner (10) Patent No.: US 10,583,266 B2
(45) Date of Patent: Mar. 10, 2020

(54) BI-LEVEL POSITIVE AIRWAY PRESSURE DEVICE

(71) Applicant: MERCURY ENTERPRISES, INC., Clearwater, FL (US)

(72) Inventor: Jeffrey B. Ratner, Pinellas Park, FL (US)

(73) Assignee: MERCURY ENTERPRISES, INC., Clearwater, FL (US)

( * ) Notice: Subject to any disclaimer, the term of this patent is extended or adjusted under 35 U.S.C. 154(b) by 478 days.

(21) Appl. No.: 15/582,980

(22) Filed: May 1, 2017

(65) Prior Publication Data

US 2017/0232224 A1    Aug. 17, 2017

Related U.S. Application Data

(63) Continuation-in-part of application No. 14/853,079, filed on Sep. 14, 2015, now Pat. No. 10,258,759.

(60) Provisional application No. 62/050,554, filed on Sep. 15, 2014.

(51) Int. Cl.
*A61M 16/00* (2006.01)
*A61M 16/20* (2006.01)

(52) U.S. Cl.
CPC ........ *A61M 16/208* (2013.01); *A61M 16/207* (2014.02); *A61M 2016/003* (2013.01); *A61M 2016/0015* (2013.01); *A61M 2016/0027* (2013.01); *A61M 2205/3331* (2013.01)

(58) Field of Classification Search
CPC .............. A61M 16/208; A61M 16/207; A61M 2016/003; A61M 2016/0027; A61M 2205/3331

See application file for complete search history.

(56) References Cited

U.S. PATENT DOCUMENTS

| 6,253,764 B1 * | 7/2001 | Calluaud ............... A61M 16/20 128/204.18 |
| 10,258,759 B2 * | 4/2019 | Ratner ................ A61M 16/208 |
| 2014/0150793 A1 | 6/2014 | Douglas et al. |

* cited by examiner

*Primary Examiner* — Steven O Douglas
(74) *Attorney, Agent, or Firm* — Larson & Larson, P.A.; Frank Liebenow; Justin P. Miller (57) ABSTRACT

A bi-level positive airway pressure device includes a housing that has a patient port for connecting to an airway of a patient. Within the housing is a device that generates a positive airway pressure directed towards to patient port. Also within the housing is a system that detects exhalation (by a patient that is connected to the patient port) that enters into the patient port. Responsive to detecting exhalation, a blocking device occludes the device that generated positive airway pressure, thereby reducing or stopping the positive airway pressure. Upon the system detects abatement of exhalation, the blocking device is operated to no longer occlude the device for generating positive airway pressure, thereby providing positive airway pressure to the patient port.

14 Claims, 10 Drawing Sheets

BI-LEVEL POSITIVE AIRWAY PRESSURE DEVICE

CROSS-REFERENCE TO RELATED APPLICATION

This application is a continuation-in-part of U.S. patent application Ser. No. 14/853,079 filed Sep. 14, 2015 which in turn claims the benefit of U.S. provisional application No. 62/050,554 filed on Sep. 15, 2014, the disclosure of both are incorporated by reference.

FIELD

This invention relates to the field of medicine and more particularly to an apparatus for delivering bi-level positive airway pressure.

BACKGROUND

Patients (e.g. mammals such as humans) having respiratory issues such as chronic obstructive pulmonary disease (COPD), sleep apnea, etc., often require assistance in filling their lungs with air, or inhalation. There exist devices that are interfaced to a patient's airway for providing such assistance by injecting a positive airway pressure towards and into the patient' airway, thereby assisting that patient with inhalation.

One type of device for providing such assistance is a Continuous Positive Airway Pressure (CPAP) device as described in, for example, U.S. Pat. No. 4,944,310. Continuous Positive Airway Pressure devices generally provide a gas pressure that is slightly greater than ambient air pressure into the patient's airway. Continuous Positive Airway Pressure devices work well for certain patients, but patients that have poor lung capability often find it harder to exhale due to the constant added pressure directed into the patient's air passages by the Continuous Positive Airway Pressure device. This is because the Continuous Positive Airway Pressure device continues to provide positive air pressure, even while the patient is exhaling.

Bi-level Positive Airway Pressure devices address this issue of exhalation as described above by detecting when the patient is exhaling and reducing the positive airway pressure until the patient completes exhalation and starts inhalation. In such, there are two different positive airway pressures delivered (hence bi-level), a higher positive airway pressure while the patient inhales and a lower positive airway pressure (e.g., atmospheric pressure) while the patient exhales.

To accomplish the bi-level positive airway pressure delivery, Bi-level Positive Airway Pressure devices of current have electrical transducers that senses when the patient is exhaling and an electrical circuit that receives an electrical signal from the transducers and responsive to that signal, modulates the positive airway pressure between two values. For example, U.S. Pat. Pub. 20140150793 describes such a Bi-level Positive Airway Pressure device that has a flow sensor connected to a controller. This device has a blower for providing the positive airway pressure. Upon detecting that a patient is exhaling, the controller sets the blower to operate at a lower speed (or off), thereby reducing the positive airway pressure until the patient stops exhaling, at which time the controller detects the end of the exhalation and restarts the blower.

The above-described Bi-level Positive Airway Pressure devices are known to function well, especially with patients that have very little lung capacity. Unfortunately, many such patients are not limited to bed rest and wish to be mobile. It is known to provide the pressure component for positive airway pressure by a portable device, typically portable Continuous Positive Airway Pressure (CPAP) devices. Such devices typically derive the pressure component for positive airway pressure from a small battery operated pump or through a compressed gas cylinder (e.g. air, oxygen, etc.). It is possible, especially if made small and light enough to be carried by the patient. The sensors, the connections to the sensors, and the added electronics make portability hard to accomplish, especially if a compressed gas tank is utilized. Further, the issues related to battery charge maintenance become an issue. Further, due to the electronic components, power supplies, etc., it is difficult to dispose of such a device, making single-use devices out of the question. Therefore, such devices are not envisioned as to be sold as disposable devices.

What is needed is a bi-level positive airway pressure system that has an entirely mechanical/pneumatic system for switching between pressures.

SUMMARY

In one embodiment, a bi-level positive airway pressure device is disclosed including a housing that has a patient port for connecting to an airway of a patient. Within the housing is a device such as a nozzle that generates a positive airway pressure directed towards to patient port. Also within the housing is a subsystem that mechanically detects exhalation (by the patient connected to the patient port) entering into the patient port. Responsive to detecting exhalation, a blocking device occludes (moves in front of) the device that generates positive airway pressure. This reduces or stops the positive airway pressure until the subsystem no longer detects exhalation, at which time the blocking device is operated (moved away) to no longer occlude the device for generating positive airway pressure, thereby providing positive airway pressure to the patient port during, for example, inhalation.

In another embodiment, a bi-level positive airway pressure device is disclosed including a housing having a patient port for connecting to an airway of a patient. The bi-level positive airway pressure device has mechanisms for generating a positive airway pressure directed towards the patient port and mechanisms for detecting exhalation entering into the patient port. Mechanisms are provided for selectively blocking the positive airway pressure, blocking the positive airway pressure when the mechanism for detecting exhalation detects exhalation (e.g. the patient breaths out), inhalation (e.g. the patient breaths in) or absence of breath, thereby making it easier for the patient to exhale, etc.

In another embodiment, a bi-level positive airway pressure device is disclosed including a housing having a patient port for connecting to an airway of a patient. A nozzle generates a positive airway pressure directed towards the patient port. The nozzle is positioned near an end of the housing distal from the patient port. A mechanical device for detecting an exhalation flow entering into the patient port is coupled to a occluding member such that upon detection of the exhalation flow, the mechanical device causes the occluding member to block the nozzle, thereby abating the positive airway pressure.

In another embodiment, a bi-level positive airway pressure device is disclosed including a housing having a patient port at one end for interfacing to an airway of a patient. A nozzle that is interfaced to a supply of gas generates a positive airway pressure in a direction aimed at the patient port. The nozzle situated at an end of the housing distal from the patient port and the nozzle is directed towards the patient port. An occluding member is movably positioned between the nozzle and the patient port and is positionable in at least two positions. A first position blocks the positive airway pressure and a second position allows flow of the positive airway pressure to the patient port. A gas jet is initially aimed at a first port and during exhalation; the gas jet deflects to be aimed at a second port. The first port is in fluid communications with a first mechanical device that moves the occluding member to the second position when the first mechanical device (e.g., diaphragm) receives pressure from the gas jet, thereby enabling the positive airway pressure. The second port is in fluid communications with a second mechanical device that moves the occluding member to the first position when the second mechanical device (e.g., diaphragm) receives pressure from the gas jet, thereby abating the positive airway pressure when the exhalation flow is detected.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Figure 1A:
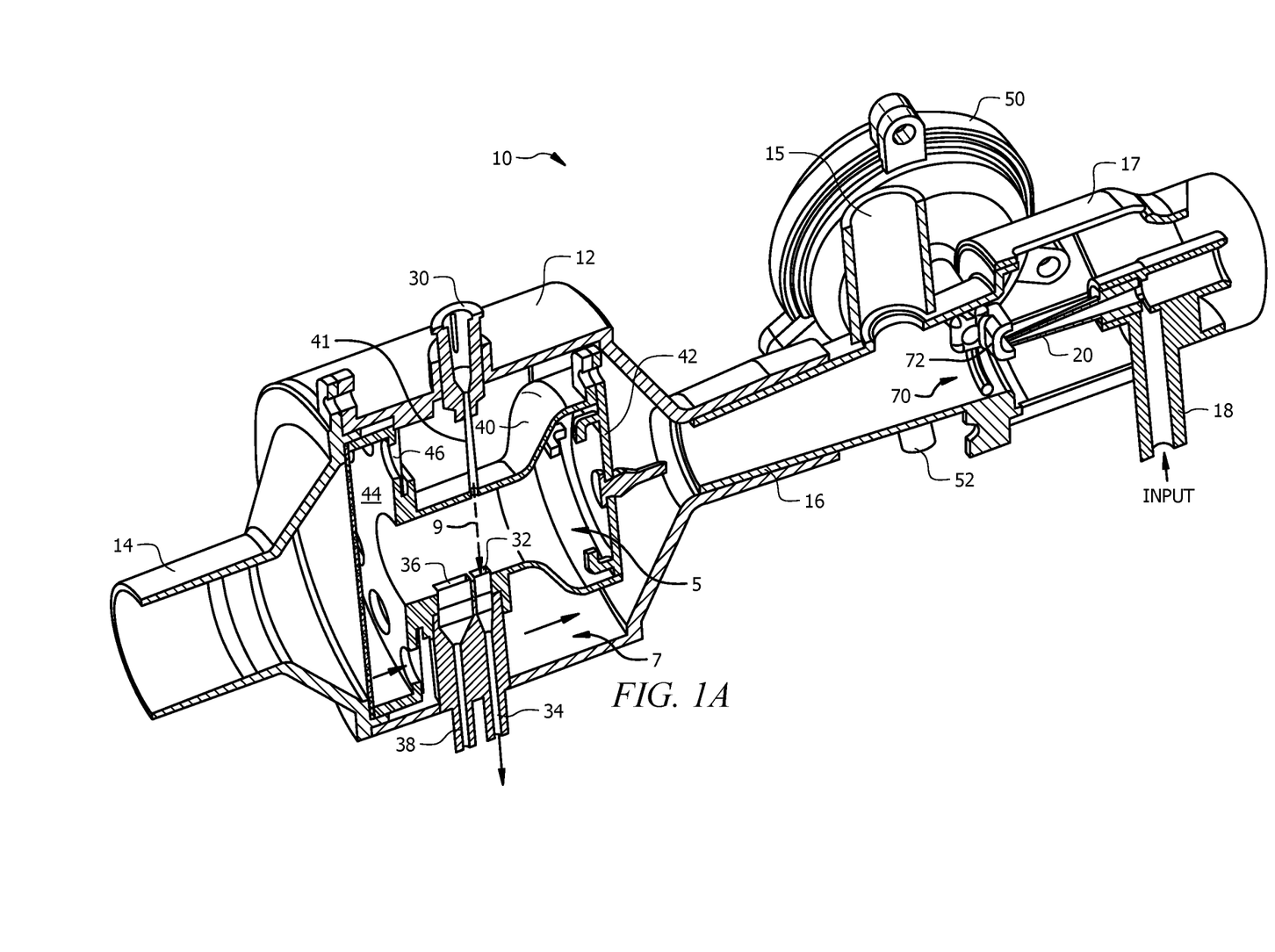
FIGS. 1A and 1B illustrate cut-away views of a mechanical bi-level positive airway pressure system.
Figure 1B:
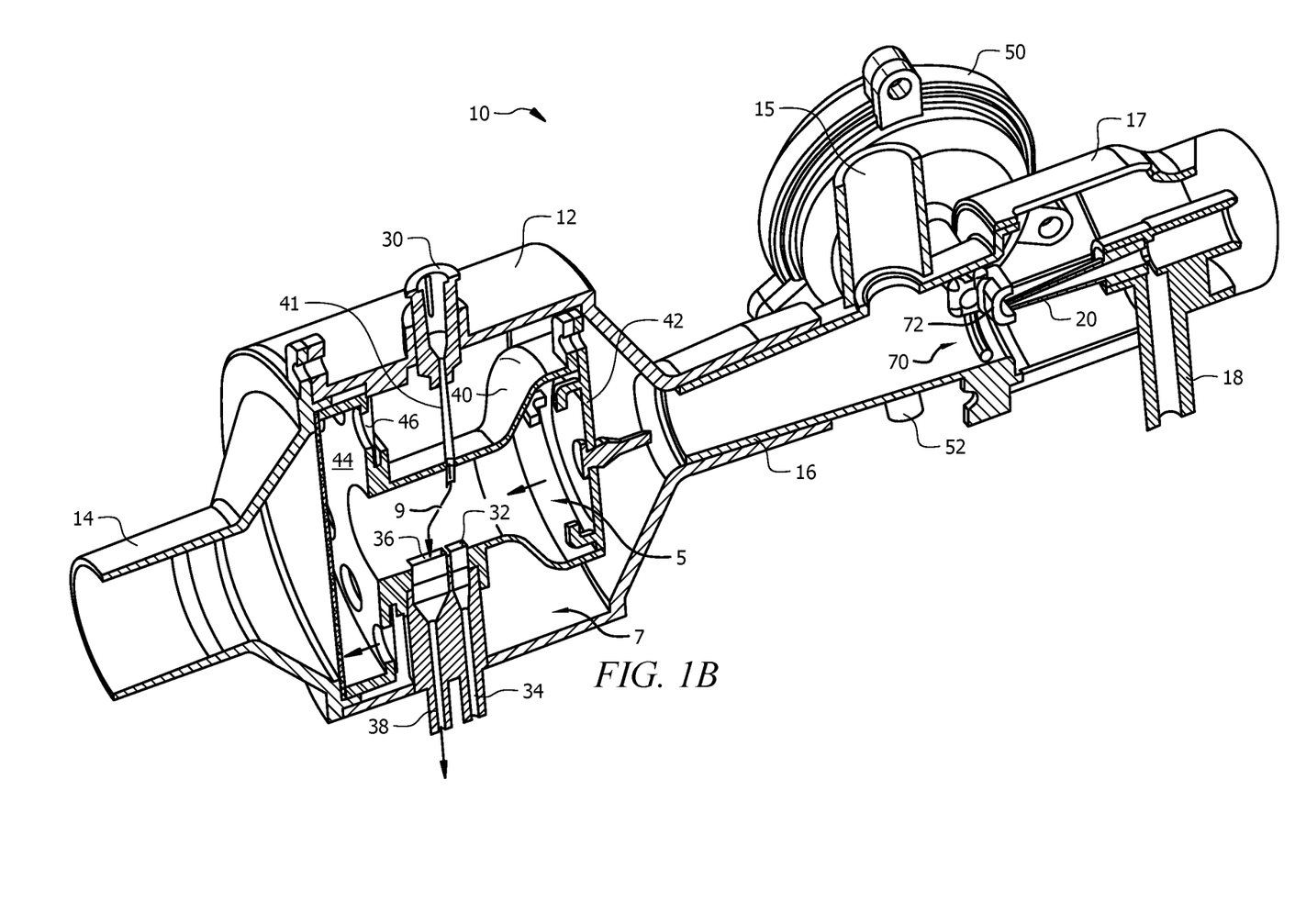

Referring to FIGS. 1A and 1B, cut-away views of a mechanical bi-level positive airway pressure system 10 are shown. The principles of operation of the bi-level positive airway pressure system 10 are understandable from FIGS. 1A and 1B.

In FIGS. 1A and 1B, the patient airway (not shown) is interfaced to the patient port 14 by any way known in the industry such as by a nasal cannula, facemask, endotracheal tube, etc.

As shown in FIG. 1A, during exhalation, the flow of air from the patient travels through the outer chamber 7 of the detection section 12 as indicated by the air flow arrow. A first one-way valve 44/46 allows flow in the exhalation direction through the outer chamber (indicated by an arrow) while a second one-way valve 40/42 precludes flow through the inner chamber 5 defined by an inner structure member 40 of the second one-way valve 40/42.

As shown in FIG. 1B, during inhalation, the one-way valves 44/46/40/42 operate in an opposing fashion, in that, the flow of air from the positive pressure nozzle 20 (optionally along with atmospheric air) travels through the inner chamber 5 of the detection section 12 as indicated by the inhalation air flow arrow in FIG. 1B. The first one-way valve 44/46 blocks flow in the inhalation so there is no flow through the outer chamber 7 while the second one-way valve 40/42 allows flow through the inner chamber 5 as indicated by the inhalation flow arrow. The positive pressure nozzle 20 is provided with gas under pressure from a positive pressure input port 18.

In FIGS. 1A and 1B, there is a pressurized gas input 30 that is connected to a source a pressurized gas (e.g. air, oxygen, etc.—not shown). A jet 9 of gas flows out of a gas stream nozzle 41 and crosses the inner chamber 5 falling onto one of the receptor channels 32/36. As shown in FIG. 1A, when the patient is not inhaling (e.g., exhaling or at rest), the jet 9 of gas flows directly across the inner chamber 5 and into the first receptor channel 32. The first receptor channel 32 is fluidly interfaced to a first port 34 that is connected to an input 52 of a first pressure-to-movement conversion device 50 that is explained later.

As shown in FIG. 1B, when the patient is inhaling, the jet 9 of gas flowing across the inner chamber 5 is deflected and flows into the second receptor channel 36. The second receptor channel 36 is fluidly interfaced to a second port 38 which, in turn, is connected to an input 62 of a second pressure-to-movement conversion device 60 (see FIG. 2) which is explained later. In other embodiments, the jet 9 of gas is deflected or blocked by a device linked to a diaphragm, in particular for patients with very weak lung capacity.

Figure 4:
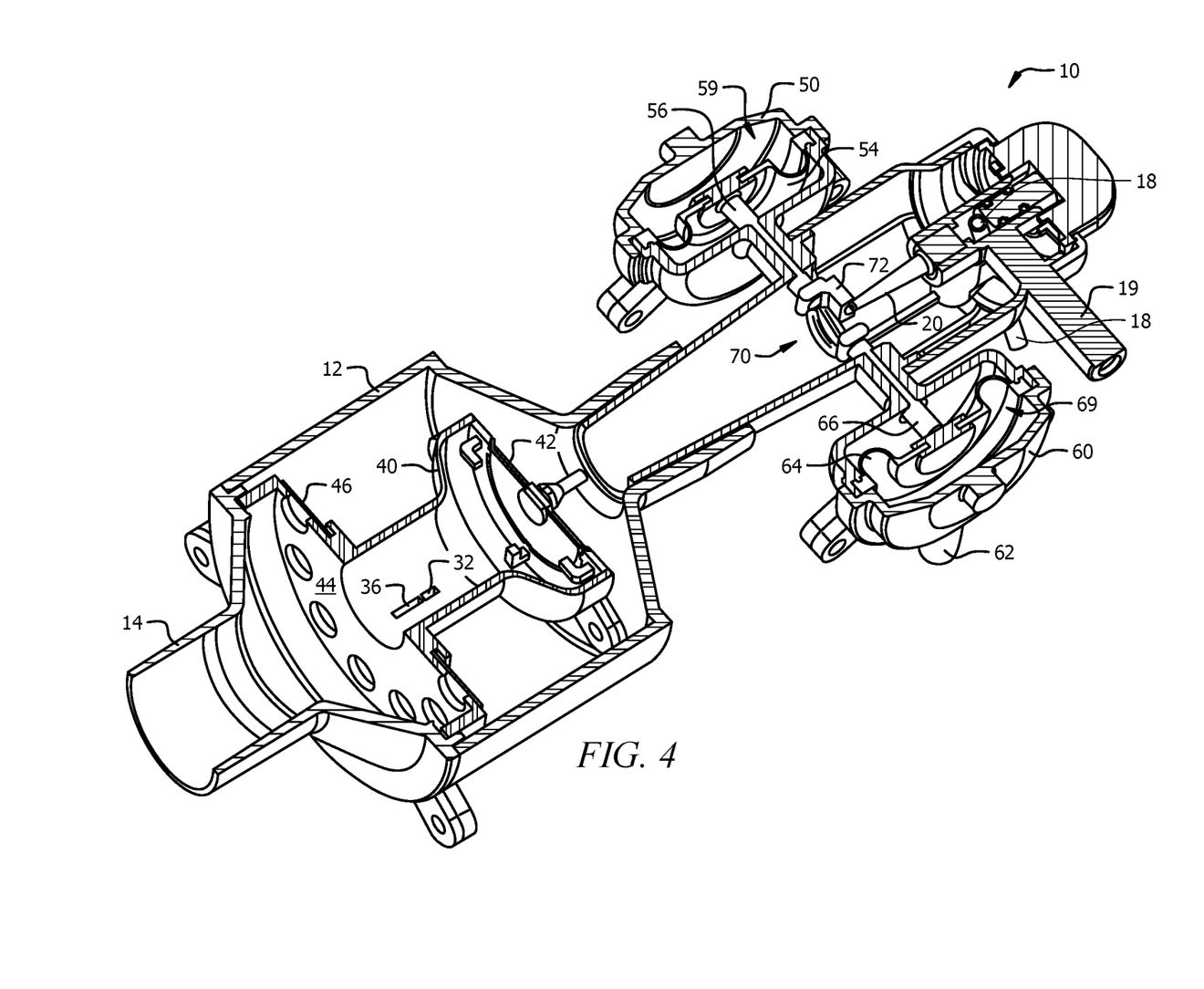
FIG. 4 illustrates another cut-away view of the mechanical bi-level positive airway pressure system.

The first pressure-to-movement conversion device 50 and the second pressure-to-movement conversion device 60 (see FIG. 2) push a movable occlusion device 70 that has an occluding member 72. The occluding member 72 is moved in front of the positive pressure nozzle 20 while the patient is not inhaling, thereby blocking gas pressure that continuously flows out of the positive pressure nozzle 20 until the patient starts to inhale. When the patient starts to inhale, the jet 9 of gas flowing across the inner chamber 5 is deflected and flows into the second receptor channel 36, which is in fluid communications with the second pressure-to-movement conversion device 60 that converts the gas pressure into a movement of the occluding member 72. The occluding member 72 moves to a position in which the gas pressure from the positive pressure nozzle 20 is no longer blocked. This provides positive pressure to the patient, helping the patient inhale. When the patient stops inhaling, the jet 9 of gas flowing across the inner chamber 5 relaxes and flows into the first receptor channel 32, which is in fluid communications with the first pressure-to-movement conversion device 50. The first pressure-to-movement conversion device 50 converts the gas pressure into a movement of the occluding member 72 to a position in which the gas pressure from the positive pressure nozzle 20 is blocked. This results in reducing the positive pressure and allowing for exhalation by the patient without needing to overcome the positive pressure. An example of pressure-to-movement conversion devices 50/60 and the movable occlusion device 70, including the occluding member 72 is shown in FIG. 4. It is fully anticipated that in some embodiments, a single pressure-to-movement conversion device operates on a pressure from one or the other of the first receptor channel 32 or the second receptor channel 36 using a resilient member or the resiliency of the diaphragm to return the occlusion device to the correct position after abatement of the gas pressure. Therefore, it is fully anticipated that in some embodiments, a single pressure-to-movement conversion device 50/60 is used and resilient force is used to return the occluding member 72 back to a resting position. For example, a single pressure-to-movement conversion device 60 fluidly interfaced to the second receptor channel, in which the single pressure-to-movement conversion device 60 has a resilient diaphragm in which the resilient diaphragm works to pull the occluding member 72 into a resting position. When the patient inhales, the jet 9 of gas flowing across the inner chamber 5 bends and flows into the second receptor channel 36, thereby placing air pressure upon the resilient diaphragm, thereby overcoming the resilient force of the diaphragm and moving the occluding member 72 away from the positive pressure nozzle 20, providing positive pressure to the patient. When the patient stops inhaling, the jet 9 of gas flowing across the inner chamber 5 retorts to its natural flow and no longer enters the second receptor channel 36 and the resilient force of the diaphragm moves the occluding member 72 in front of the positive pressure nozzle 20, allowing the patient easier of exhalation.

A pressure relief valve 15 is provided to allow atmospheric air to flow out of the bi-level positive airway pressure system 10, allowing internal pressure to escape when a specific pressure is exceeded. Details of the pressure relieve valve 15 are not shown for brevity and clarity reasons, though a typical pressure relief valve includes a spring-loaded ball valve, such that when pressure exceeds the force of the spring, the ball is pushed away from a seat, allowing pressure to escape.

In some embodiments, the intermediate channel 16 between the positive pressure nozzle 20 and the detection section 12 is tapered to a narrower diameter to increase the velocity of the gas as it moves toward the patient. In some embodiments, the taper is a linear taper as shown in the figures.

Figure 2:
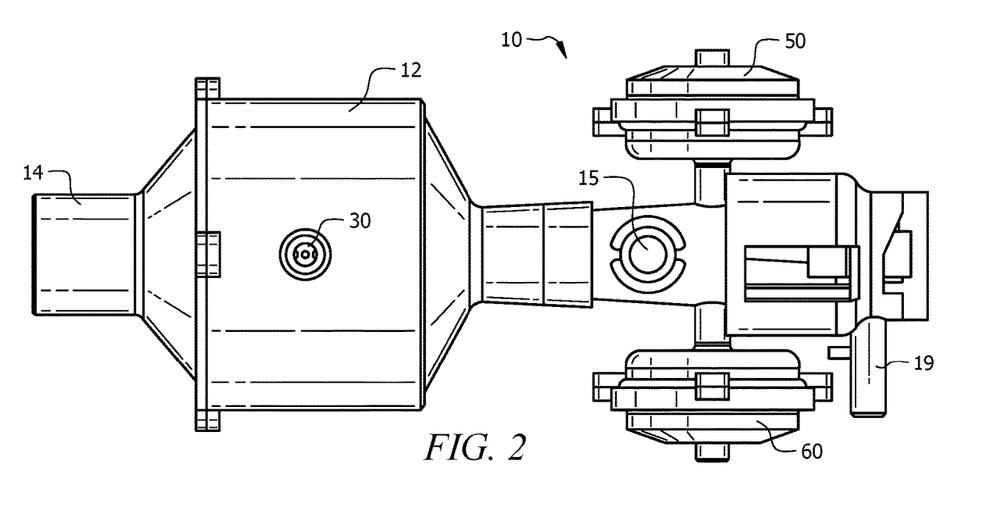
FIGS. 2 and 3 illustrate plan views of the mechanical bi-level positive airway pressure system.
Figure 3:
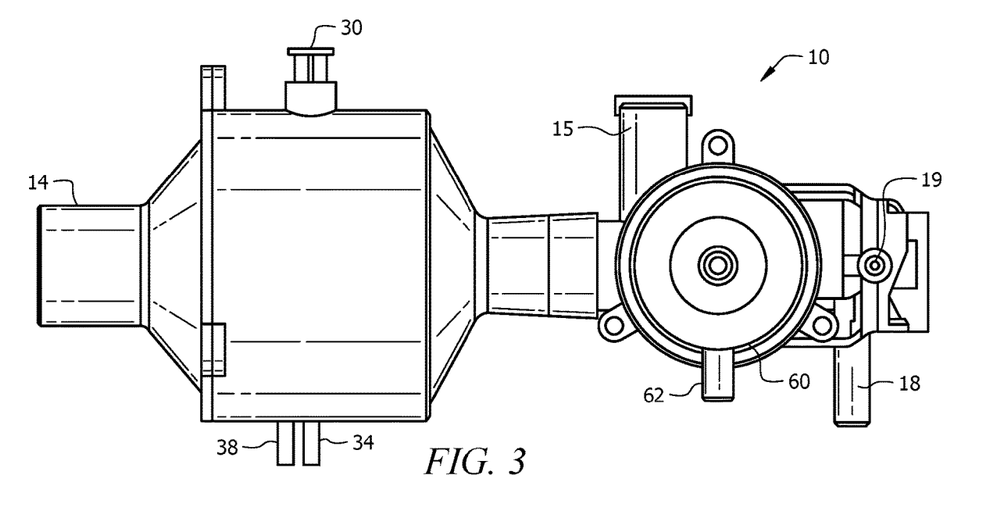

Referring to FIGS. 2 and 3, plan views of the mechanical bi-level positive airway pressure system 10 are shown. In this view, an exemplary outside enclosure including the detection section 12 is visible as well as both pressure-to-movement conversion devices. Gas, under pressure, is connected to the pressurized gas input 30 to create the jet 9 of gas. Gas, under pressure, is also connected to the positive pressure input port 18. Although it is anticipated that the same source of pressurized gas is provided to both the pressurized gas input 30 and the positive pressure input port 18, it is also anticipated that in other embodiments, different sources of gas are used, in some embodiments being the same gas under different pressures and in some embodiments being different gases.

Referring to FIG. 4, another cut-away view of the mechanical bi-level positive airway pressure system 10 is shown. In this view, construction of exemplary pressure-to-movement conversion devices 50/60 and the movable occlusion device 70, including the occluding member 72, is visible.

Each of the exemplary pressure-to-movement conversion devices 50/60 has a diaphragm 54/64 that is interfaced to a respective push rod 56/66. Air pressure from the respective ports 34/38 enter the pressure-to-movement conversion devices 50/60 from respective inputs 52/62 (see FIG. 5) that are in fluid communications with the outer chambers 59/69 surrounding the diaphragms 54/64. When air pressure enters the respective outer chamber 59/69, the air pressure pushes against the respective diaphragm 54/64, therefore, moving the respective push rods 56/66 in a direction towards the movable occlusion device 70. The push rods 56/66 are coupled to the movable occlusion device 70, thereby moving the occluding member 72 either in front of the positive pressure nozzle 20 (during exhalation) or away from the positive pressure nozzle 20 (during inhalation).

Note that the exemplary pressure-to-movement conversion devices 50/60 are examples and many other devices are anticipated that perform similar functions in various ways, including using pistons, etc. Again, it is noted that it is anticipated that in some embodiments, only a single pressure-to-movement conversion device 50/60 is present.

Figure 5:
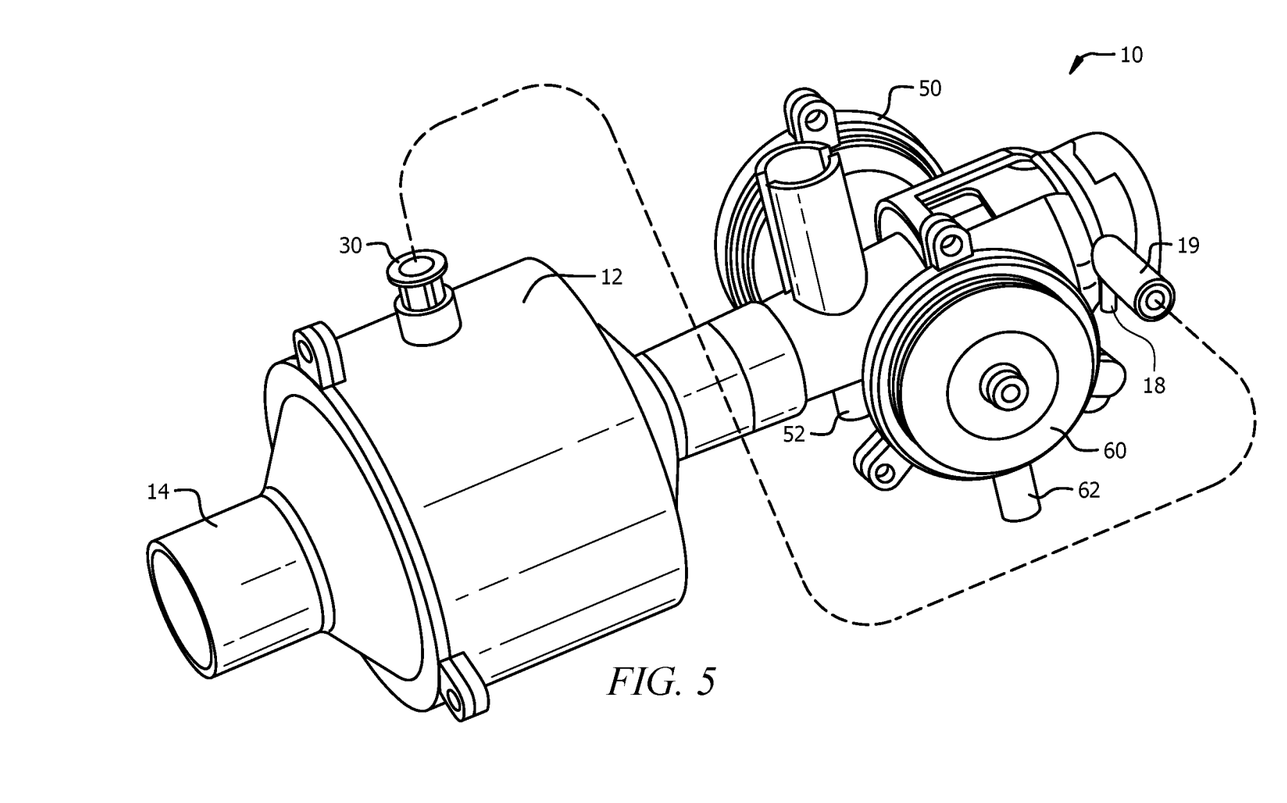
FIG. 5 illustrates a perspective view of the mechanical bi-level positive airway pressure system.

Referring to FIG. 5, a perspective view of the mechanical bi-level positive airway pressure system 10 is shown. It is anticipated that, for example, gas tubing connects both the pressurized gas input 30 and the positive pressure input port 18 to a source of pressurize gas (not shown for brevity reasons). It is also anticipated that the first port 34 is connected to the input 52 of a first pressure-to-movement conversion device 50 by a section of gas tubing (not shown for brevity reasons). Likewise, the second port 38 is connected to the input 62 of a second pressure-to-movement conversion device 60 by another section of gas tubing (not shown for brevity reasons). In alternate embodiments, it is equally anticipated that the first port 34 is directly connected to the input 52 of a first pressure-to-movement conversion device 50 through a channel formed in the body of the bi-level positive airway pressure system 10. Likewise, the second port 38 is directly connected to the input 62 of a second pressure-to-movement conversion device 60 through another channel formed in the body of the bi-level positive airway pressure system 10.

Figure 6A:
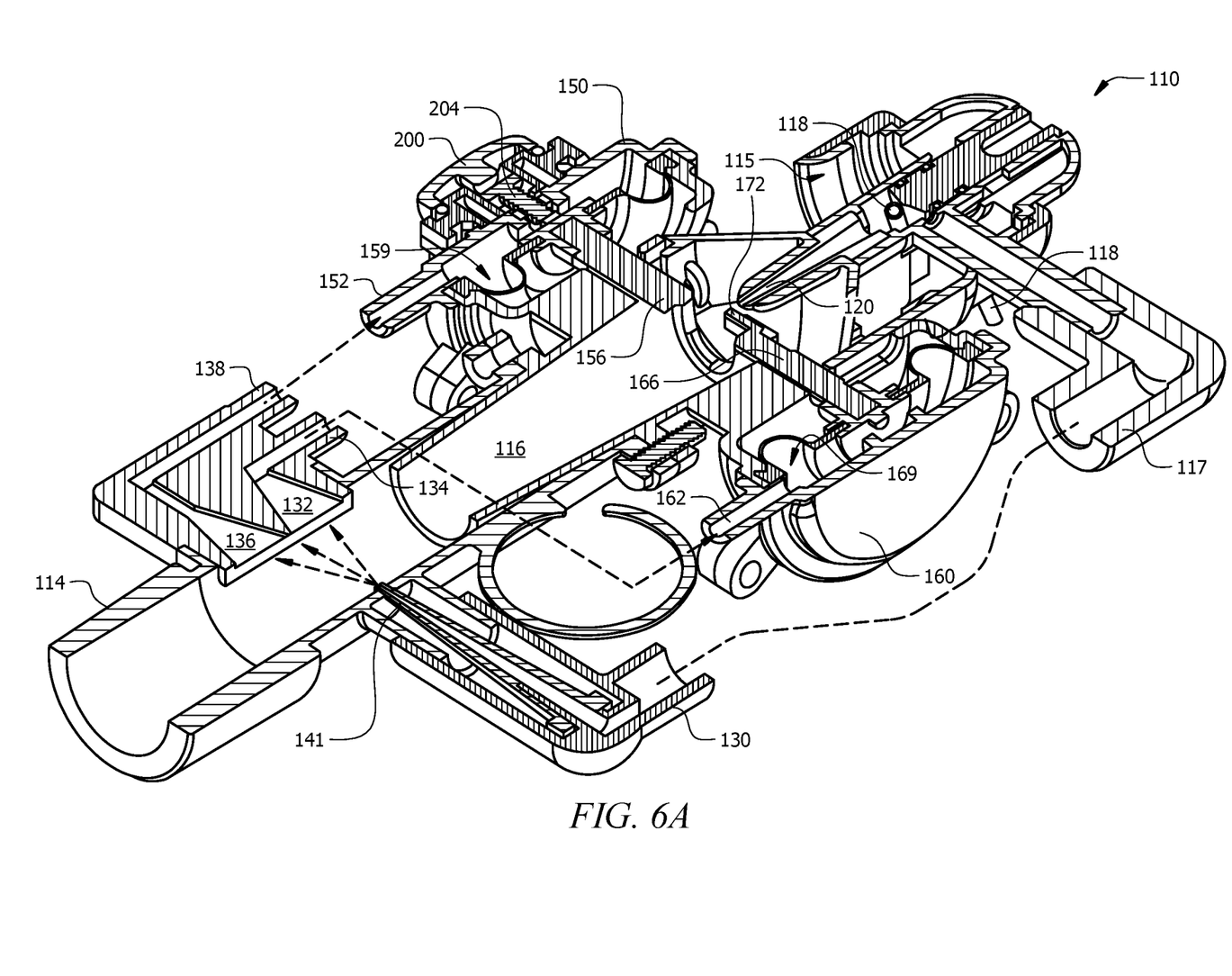
FIGS. 6A, 6B and 6C illustrate cut-away perspective views of a second mechanical bi-level positive airway pressure system.
Figure 6B:
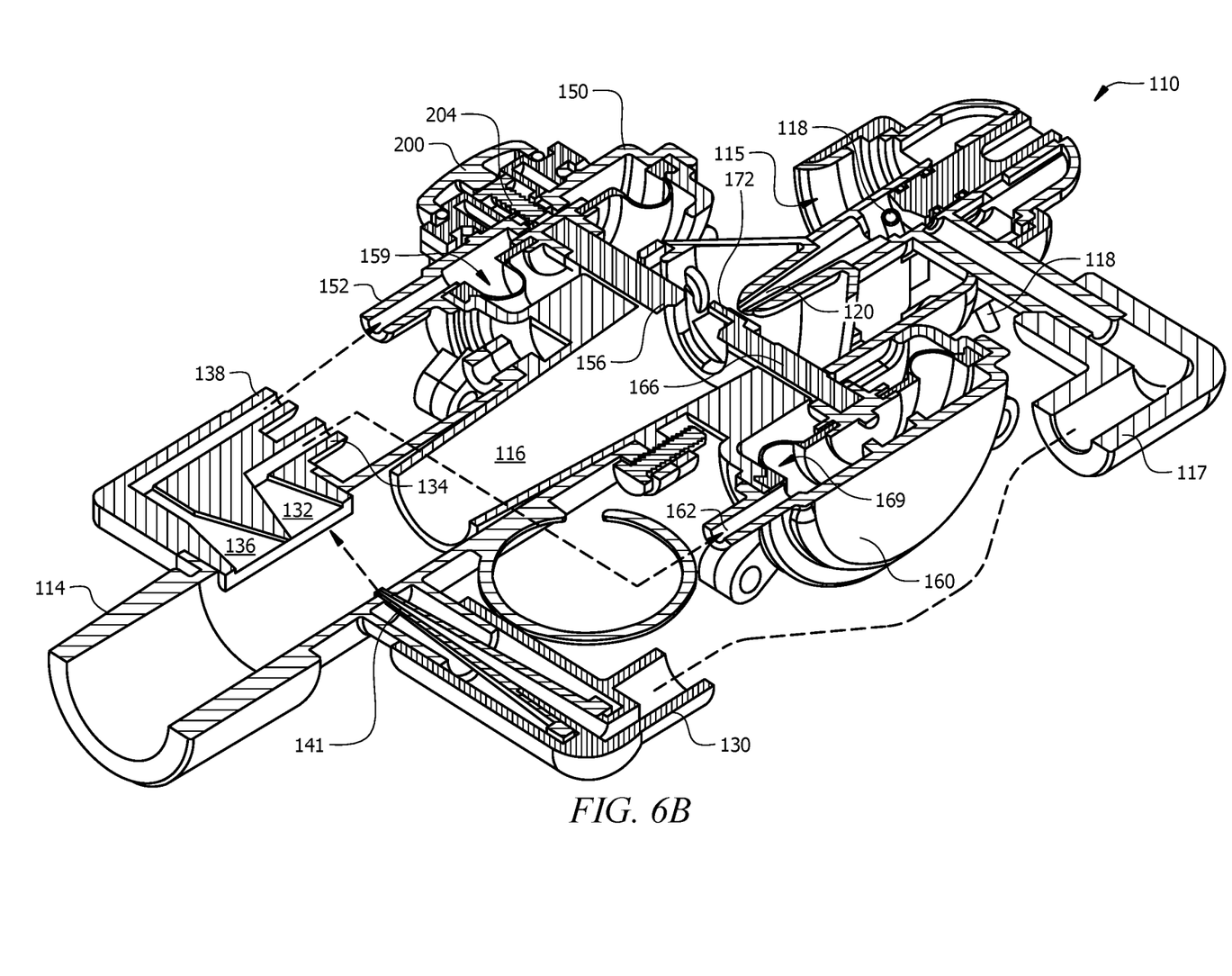
Figure 6C:
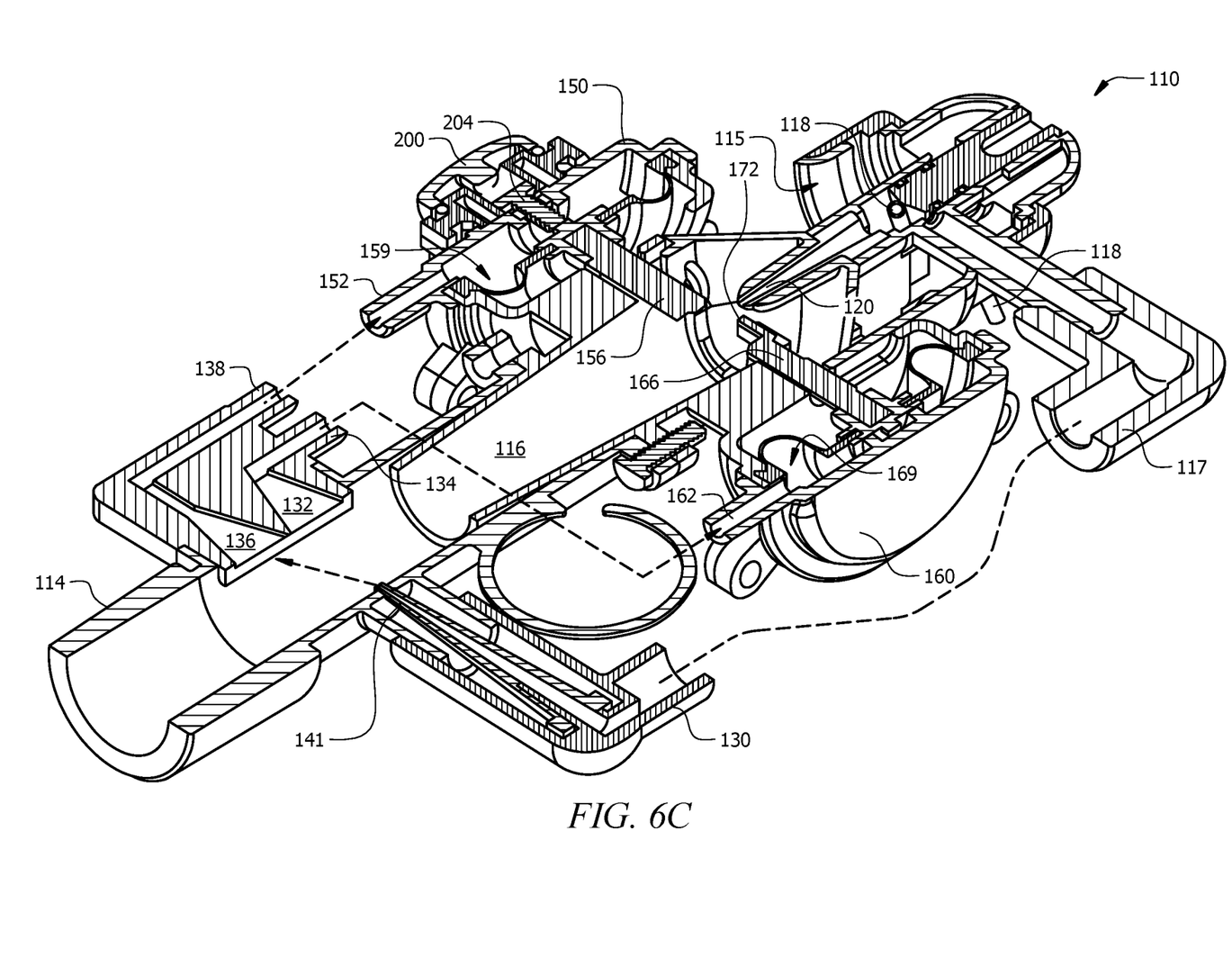

FIGS. 6A, 6B and 6C illustrate cut-away perspective views of a second mechanical bi-level positive airway pressure system 110. The second mechanical bi-level positive airway pressure system 110 functions similar to the mechanical bi-level positive airway pressure system 10 described previously without the need for one-way valves.

In FIGS. 6A, 6B and 6C, the patient airway (not shown) is interfaced to the patient port 114 by any way known in the industry such as by a nasal cannula, facemask, endotracheal tube, etc.

The intent of any bi-level positive airway pressure system is to provide assisted inhalation to a patient during inhalation while reducing this assistance during exhalation to make it easier to exhale.

The mechanical bi-level positive airway pressure system 110 as shown in FIGS. 6A, 6B and 6C accomplish such through a feedback system that provides positive air pressure until the patient exhales, at which time the source of the positive air pressure is blocked, thereby allowing the patient to exhale.

The components of the second mechanical bi-level positive airway pressure system 110 are shown in FIG. 6A. The breath detection sub-system includes a nozzle 141 that is in fluid communications with a source of air pressure connected to a port 130. As shown in FIG. 6A, a jet of gas crosses the path of the breath to/from the patient port 114. At rest, the jet of gas flows directly across the patient port 114 and enters both receptor channels 132/136 as depicted by the center arrow (e.g. equally or approximately equally). In some embodiments, the jet of gas is biased toward the forward receptor channel 136. In some embodiments, the jet of gas is biased toward the rear receptor channel 132. In other embodiments, the jet of gas is not biased towards either the forward receptor channel 136 or the rear receptor channel 132.

As the patient inhales, the jet of air bends more toward the forward receptor channel 136. As the patent exhales, the jet of air bends more toward the rear receptor channel 132.

The forward receptor channel 136 has a first connector 138 that is in fluid communications with a first diaphragm 159 through a first diaphragm port 152. For example, a tube 137 (see FIG. 7) or hose that connects the first connector 138 with the first diaphragm port 152.

The rear receptor channel 132 has a second connector 134 that is in fluid communications with a second diaphragm 169 through a second diaphragm port 162. For example, a second tube 135 or hose connects the second connector 134 with the second diaphragm port 162.

The first diaphragm 159 is in a first housing 150 and the second diaphragm 169 is in a second housing 160. The first diaphragm 159, when supplied with gas pressure, pushes on a first displacement rod 156 and the second diaphragm 169, when supplied with gas pressure, pushes in an opposite direction on a second displacement rod 166. The first displacement rod 156 is interfaced to the second displacement rod 166 creating a push-push system where the first diaphragm 159 pushes the displacement rods 156/166 in one direction and the second diaphragm 169 pushes the displacement rods 156/166 in the opposite direction. The displacement rods 156/166 move an occluding member 172 accordingly, either away from the source of airway pressure 120 during inhalation or in front of and blocking the source of airway pressure 120 during exhalation.

In some embodiments, a bias adjustment 200 is provided. The bias adjustment 200 adjusts an offset of the occluding member 172 through, for example, a screw mechanism. By turning the bias adjustment 200 in one direction, the occluding member 172 is moved slightly out of occlusion of the source of airway pressure 120 and by turning the bias adjustment 200 in the opposite direction, the occluding member 172 is moved slightly further into occlusion of the source of airway pressure 120.

In some embodiments, the intermediate channel 116 between the source of airway pressure 120 and the patient port 114 is tapered (e.g. frustum-shaped) to a narrower diameter to increase the velocity of the gas as it moves toward the patient. In some embodiments, the taper is a linear taper as shown in the figures. The taper of the intermediate channel 116 accelerates the flow of air and provide greater positive airway pressure utilizing less pressurized gas from a source of gas connected to the gas source port 118.

Note that it is anticipate, though not required, that both the gas source port 118 and the port 130 be connected to the same source of pressurized gas, such as an oxygen tank, hospital oxygen port, etc.

Note also that, in some embodiments, a single, first diaphragm 159 coupled to a single forward receptor channel 136. In this, the resiliency of the single, first diaphragm 159 returns the occluding member 172 to occlude the source of airway pressure 120 when the exhalation occurs.

Starting from the position shown in FIG. 6A, when exhalation occurs as shown by exhalation arrows in FIG. 6B, the flow of air from the patient flows into the mechanical bi-level positive airway pressure system 110 from the patient port 114 as indicated by the jet flow arrow in FIG. 6B. The flow of air from the patient deflects the jet of air from the nozzle 141 such that the jet of air is received by the rear receptor channel 132. The rear receptor channel 132 is in fluid communication with the second diaphragm 169 that pushes the second displacement rod 166, moving the occluding member 172 to a position where it blocks the source of airway pressure 120. The result is that the occluding member 172 abates or reduces the positive airway pressure provided to the patient port 114, making it easier for exhalation.

Now, referring to FIG. 6C, when inhalation occurs, the flow of air from the mechanical bi-level positive airway pressure system 110 towards the patient port 114 as indicated by the air flow arrow in FIG. 6C. The flow of air towards the patient port 114 deflects the jet of air from the nozzle 141 such that the jet of air is now received by the forward receptor channel 136. The forward receptor channel 136 is in fluid communication with the first diaphragm 159 that pushes the first displacement rod 156. This moves occluding member 172 to a position where it does not block the source of airway pressure 120, thereby providing the positive airway pressure to the patient port 114, making it easier for inhalation.

Exhaust port(s) 115 (see FIG. 8) are provided to allow atmospheric air to flow in/out of the bi-level positive airway pressure system 110, allowing the exhalation gases to escape and allowing fresh air to enter during inhalation.

Figure 7:
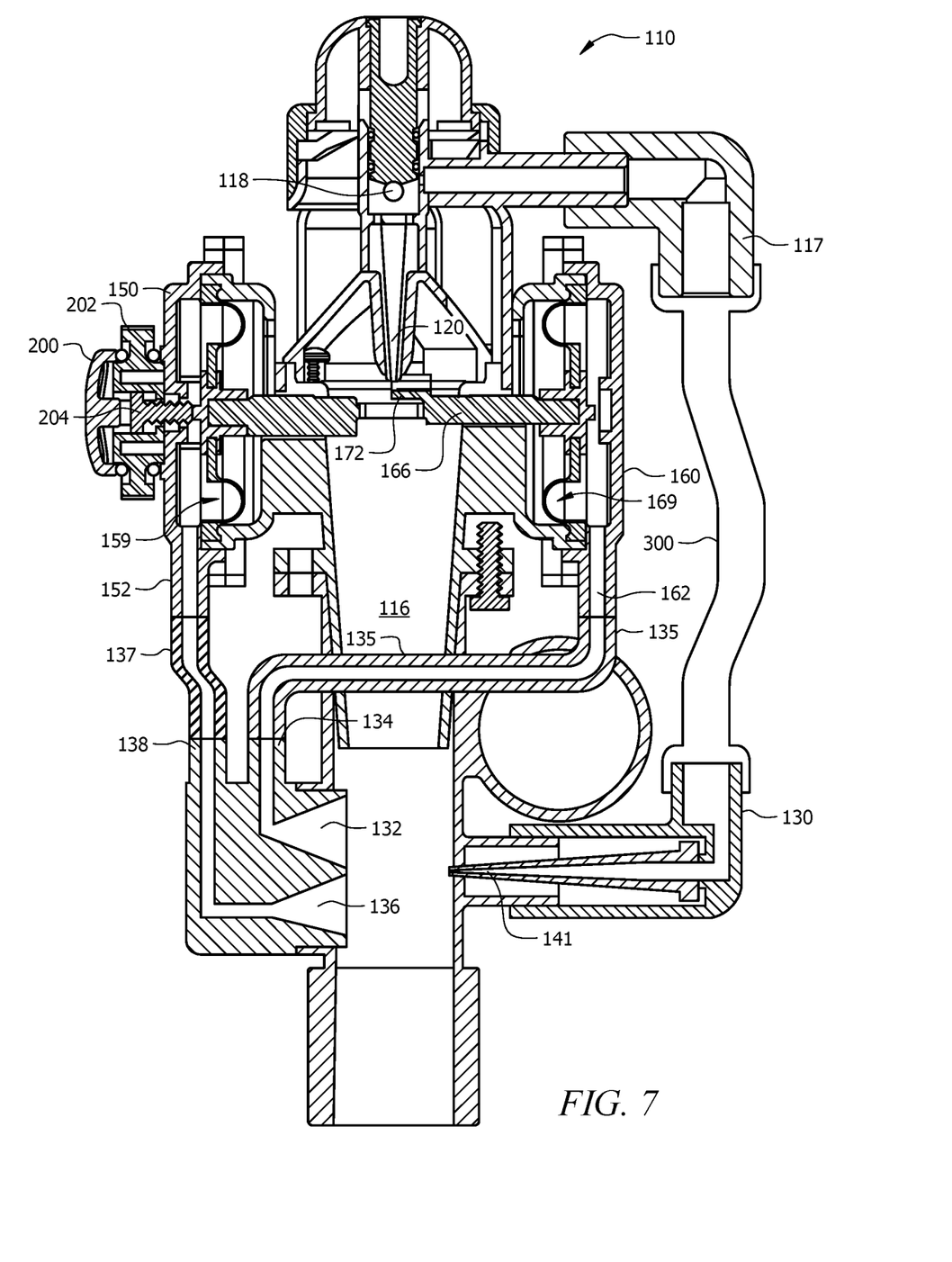
FIG. 7 illustrates a cut-away plan view of the second mechanical bi-level positive airway pressure system.

FIG. 7 illustrates a cut-away plan view of the second mechanical bi-level positive airway pressure system 110. In this view, the bias adjustment 200 is shown connected to a torquing component 202 that connects to a biasing screw 204. Note that the bias adjustment mechanism 200/202/204 is optional.

Figure 8:
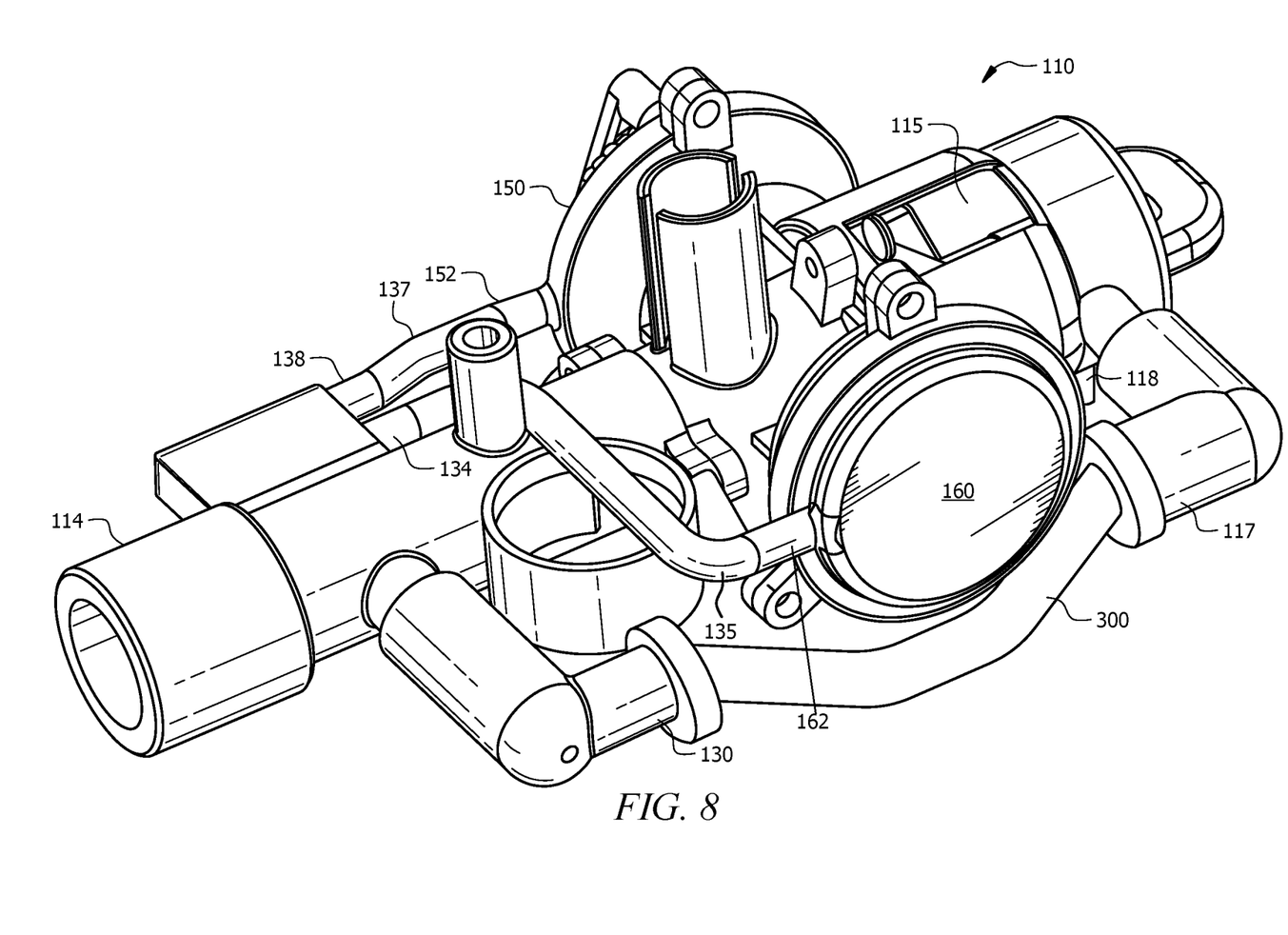
FIG. 8 illustrates a perspective view of the second mechanical bi-level positive airway pressure system.

FIG. 8 illustrates a perspective view of a physical embodiment of the second mechanical bi-level positive airway pressure system 110. As discussed, in this physical embodiment of the mechanical bi-level positive airway pressure system 110, a tube 137 connects a first connector 138 with the first diaphragm port 152 and a second tube 135 connects the second connector 134 with the second diaphragm port 162. It is also fully anticipated to interconnect such with any known mechanism including channels embedded within the housing of the mechanical bi-level positive airway pressure system 110.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A bi-level positive airway pressure device comprising:
 a housing having a patient port for connecting to an airway of a patient;
 means for generating a positive airway pressure directed towards the patient port;
 means for pneumatically detecting flow of gases into/out of the patient port;
 means for pneumatically occluding the means for generating positive airway pressure, the means for pneumatically occluding is operative to block the positive airway pressure responsive to the means for pneumatically detecting having detected a flow of gases from the patient port;
 wherein the means for pneumatically detecting comprises a nozzle emitting a jet of a gas, the jet of the gas is directed at a forward receptor channel when the flow of gases is out of the patient port, and the jet of the gas is directed at a rear receptor channel when the flow of gases is into the patient port.

2. The bi-level positive airway pressure device of claim 1, wherein the forward receptor channel is interfaced to a first diaphragm and the rear receptor channel is interfaced to a second diaphragm.

3. The bi-level positive airway pressure device of claim 2, wherein the first diaphragm upon receiving pressure from the forward receptor channel moves the means for pneumatically occluding towards an unblocking position providing positive airway pressure during inhalation and the second diaphragm upon receiving pressure from the rear receptor channel moves the means for pneumatically occluding towards a blocking position, thereby reducing positive air pressure during exhalation.

4. The bi-level positive airway pressure device of claim 1, wherein the means for generating the positive airway pressure includes a source of positive airway pressure, the source of positive airway pressure directed towards the patient port, the source of positive airway pressure connected to a source of gas pressure.

5. The bi-level positive airway pressure device of claim 4, wherein the housing has a taper between the source of positive airway pressure and the patient port, the taper linearly decreases in diameter having a greatest diameter at a point closest to the source of positive airway pressure.

6. The bi-level positive airway pressure device of claim 1, further comprising a bias adjustment mechanism, the bias adjustment mechanism moving an at-rest position of the means for pneumatically occluding.

7. A bi-level positive airway pressure device comprising:
a housing having a patient port for connecting to an airway of a patient;
a source of positive airway pressure directed towards the patient port for generating a positive airway pressure, the source of positive airway pressure positioned near an end of the housing distal from the patient port; and
means for pneumatically detecting a flow of gases entering into the patient port, the means for detecting coupled to an occluding member such that upon detection of the flow of gases entering the patient port, the means for pneumatically detecting causes the occluding member to block the source of positive airway pressure, thereby abating positive airway pressure;
wherein the means for pneumatically detecting comprises a nozzle directing a jet of a gas across the means for pneumatically detecting the flow of gases such that upon the flow of gases entering the patient port, the jet is deflected towards a rear receptor channel and in presence of flow out of the patient port, the jet is deflected towards a forward receptor channel.

8. The bi-level positive airway pressure device of claim 7, wherein the forward receptor channel is interfaced to a first diaphragm and the rear receptor channel is interfaced to a second diaphragm; the first diaphragm upon receiving pressure from the forward receptor channel moves the occluding member towards an unblocking position, and the second diaphragm upon receiving pressure from the rear receptor channel moves the occluding member towards a blocking position.

9. The bi-level positive airway pressure device of claim 7, wherein the housing has a taper between the source of positive airway pressure and the patient port, the taper linearly decreases in diameter having a greatest diameter at a point closest to the source of positive airway pressure and a smallest diameter at a second point closest to the patient port.

10. A bi-level positive airway pressure device comprising:
a housing, a patient port at one end of the housing for interfacing to an airway of a patient;
a source of positive airway pressure interfaced to a supply of gas, the source of positive airway pressure generating a positive airway pressure in a direction aimed at the patient port, the source of positive airway pressure situated at an end of the housing distal from the patient port and the source of positive airway pressure is directed towards the patient port;
an occluding member movably positioned between the source of positive airway pressure and the patient port, the occluding member positionable in at least two positions, in a first position of the two positions, the occluding member is blocking the positive airway pressure from the source of positive airway pressure and in a second position of the two positions the occluding member moves away from the positive airway pressure, thereby allowing flow of the positive airway pressure from the source of positive airway pressure to the patient port;
a nozzle aiming a jet of gas across the housing, the jet of gas deflected in a first direction into a rear receptor channel during exhalation received at the patient port, the jet of gas deflected in a second, opposite direction into a front receptor channel during inhalation pulled out of the patient port, the front receptor channel in fluid communications with a first mechanical device that moves the occluding member to the second position when the first mechanical device receives pressure from the jet of gas, thereby enabling the positive airway pressure; and the rear receptor channel in fluid communications with a second mechanical device that moves the occluding member to the first position when the second mechanical device receives pressure from the jet of gas, thereby abating the positive airway pressure when an exhalation flow is detected.

11. The bi-level positive airway pressure device of claim 10, wherein the first mechanical device is a first diaphragm and the second mechanical device is a second diaphragm; the first diaphragm upon receiving pressure from the front receptor channel moves the occluding member towards an unblocking position and the second diaphragm upon receiving pressure from the rear receptor channel moves the occluding member towards a blocking position, thereby reducing positive air pressure while exhalation flow is detected.

12. The bi-level positive airway pressure device of claim 10, wherein the housing has a taper between the source of positive airway pressure and the patient port, the taper linearly decreases in diameter having a greatest diameter at a point closest to the source of positive airway pressure and a smallest diameter at a second point closest to the patient port.

13. The bi-level positive airway pressure device of claim 10, wherein the gas jet is emitted from a nozzle from one side of an inner chamber; the front receptor channel and the rear receptor channel are positioned on an opposite side of the inner chamber.

14. The bi-level positive airway pressure device of claim 10, wherein an area of the front receptor channel is approximately equivalent to an area of the rear receptor channel.

* * * * *